(12) United States Patent
Speier et al.

(10) Patent No.: US 6,478,731 B2
(45) Date of Patent: Nov. 12, 2002

(54) ENDOSCOPE-SHEATH INTERFACE USING SCOPE LIGHT POST

(75) Inventors: Craig J. Speier, Santa Barbara, CA (US); Martin Frith, Goleta, CA (US); Justin Verkaik, Santa Barbara, CA (US)

(73) Assignee: Linvatec Corporation, Largo, FL (US)

( * ) Notice: Subject to any disclaimer, the term of this patent is extended or adjusted under 35 U.S.C. 154(b) by 133 days.

(21) Appl. No.: 09/791,959

(22) Filed: Feb. 23, 2001

(65) Prior Publication Data

US 2002/0120180 A1 Aug. 29, 2002

(51) Int. Cl.⁷ .................................................. A61B 1/04
(52) U.S. Cl. ...................................... 600/125; 600/121
(58) Field of Search ................................ 600/121, 125

(56) References Cited

U.S. PATENT DOCUMENTS

| | | | |
|---|---|---|---|
| 3,373,736 A | * | 3/1968 | Fiore et al. .................. 600/121 |
| 4,252,122 A | | 2/1981 | Halvorsen |
| 4,254,762 A | | 3/1981 | Yoon |
| 4,610,242 A | | 9/1986 | Santangelo et al. |
| 4,769,018 A | | 9/1988 | Wilson |
| 4,857,062 A | | 8/1989 | Russell |
| 4,951,977 A | | 8/1990 | Shutt |
| 5,037,386 A | | 8/1991 | Marcus et al. |
| 5,087,080 A | | 2/1992 | Shutt |
| 5,209,219 A | | 5/1993 | Hollobaugh |
| 5,261,888 A | | 11/1993 | Semm |
| 5,290,294 A | | 3/1994 | Cox et al. |
| 5,383,860 A | | 1/1995 | Lau |
| 5,456,673 A | | 10/1995 | Ziegler et al. |
| 5,730,701 A | * | 3/1998 | Furukawa et al. .......... 600/127 |
| 5,746,695 A | * | 5/1998 | Yasui et al. ................. 600/127 |
| 5,817,061 A | * | 10/1998 | Goodwin et al. ........... 604/164 |
| 5,860,913 A | * | 1/1999 | Yamaya et al. ............. 600/127 |

* cited by examiner

*Primary Examiner*—John Fox
(74) *Attorney, Agent, or Firm*—Larson & Larson, P.A.; James E. Larson

(57) ABSTRACT

A sheath is sized and configured to receive an endoscope. The sheath is provided with a housing having a proximally facing opening with a U-shaped notch. The endoscope has at the proximal end a right-angle light post which and is received closely within the U-shaped notch at the proximal opening of the sheath housing. A locking mechanism is provided including a pivotable latch having a distal end configured to be received within a notch formed on the endoscope housing distal to and diametrically opposed from the light post. The latch includes a spring tending to bias the distal portion thereof into engagement with the notch in the endoscope housing. A resilient O-ring is provided at the distal end of a recess in the sheath housing. A shoulder on the distal end of the proximal portion of the endoscope compresses the O-ring when the latch is engaged.

19 Claims, 5 Drawing Sheets

ENDOSCOPE-SHEATH INTERFACE USING SCOPE LIGHT POST

BACKGROUND OF THE INVENTION

The present invention relates to an endoscope-sheath interface using the endoscope light post. In virtually all arthroscopic procedures, the endoscope is used in combination with a sheath that attaches to the endoscope body and extends distally. The sheath serves to protect the relatively fragile endoscope and also is used to establish inflow and/or outflow channels, for irrigating fluid, surrounding the endoscope shaft. In endoscopes currently used, there exists an attachment means used to firmly secure the endoscope and sheath together axially to prevent separation during the procedure and rotationally to properly align the endoscope's direction of view with the distal opening of the sheath. Additionally, the most popular endoscopes have a endoscope/sheath attachment that is simple and convenient so that the surgeon can install the endoscope and obturator and can disconnect the endoscope and sheath during a procedure.

Numerous variations are known in the prior art concerning attachment of the endoscope to the sheath and locking the axial and rotational alignment thereof. In all of these designs known to Applicants, multiple moving parts are provided on the sheath and/or endoscope and/or complicated manufacturing operations are required on the sheath and/or endoscope in order to provide the mechanical coupling therebetween. Couplings including those known as quick connect couplings, bayonet-style couplings, quick lock couplings, and J-lock couplings are examples of the type of couplings that are known. Applicants are aware of U.S. Pat. No. 4,254,762 to Yoon, U.S. Pat. No. 4,610,242 to Santangelo et al., 5,290,294 to Cox et al., and U.S. Pat. No. 5,456,673 to Ziegler et al. In each of these patents, an endoscope system is described including an endoscope and a sheath. None of these patents teaches or suggests employing the light post as part of the connection means between the endoscope and sheath.

Multiple moving parts on the sheath add cost, can be difficult to sterilize and clean, and suffer from long-term wear and degradation. Having to provide complicated machining on the scope increases costs and introduces intricate features that are difficult to clean. It would be advantageous and desirable to provide an attachment means that achieves axial and rotational alignment in a simple manner without requiring the use of moving parts in the sheath or complicated manufacturing operations on the endoscope. It is with this need in mind that the present

SUMMARY OF THE INVENTION

The present invention relates to an endoscope-sheath interface using the endoscope light post. The present invention includes the following interrelated objects, aspects and features:

(1) In a first aspect, the present invention contemplates a sheath sized and configured to receive in installed configuration an endoscope. For this purpose, the sheath is provided with a housing having a proximally facing opening with a U-shaped notch formed therein.

(2) The endoscope has a right-angle light post formed at its proximal end having peripheral dimensions sized and configured to be received closely within the U-shaped notch at the proximal opening of the sheath housing.

(3) A locking mechanism is provided including latch means comprising a pivotable latch having a distal end configured to be received within a notch formed on the endoscope housing distal to and diametrically opposed from the light post. The latch includes spring-biasing means tending to bias the distal portion thereof into engagement with the notch in the endoscope housing.

(4) In the preferred embodiment, a resilient O-ring is provided at the distal end of a recess in the sheath housing that is designed to slidably receive the proximal end of the endoscope. A shoulder on the distal end of the proximal portion of the endoscope compresses the O-ring when the latch is engaged. The O-ring serves to seal the proximal end of the sheath to prevent fluid leakage. Additionally, the resiliency of the O-ring provides an axial force on the endoscope to effect a secure and positive engagement of the endoscope and sheath.

Accordingly, it is a first object of the present invention to provide an endoscope-sheath interface using the endoscope light post.

It is a further object of the present invention to provide such a device wherein the light post of the endoscope is used to axially and rotatably align the endoscope within a sheath.

It is a still further object of the present invention to provide such a device wherein a latch is provided on the sheath designed to latch the endoscope in position with the light post aligned in a notch formed in a proximal opening of the sheath.

It is a still further object of the present invention to provide such a device wherein an O-ring is provided to seal and spring-load the endoscope as installed within the sheath.

These and other objects, aspects and features of the present invention will be better understood from the following detailed description of the preferred embodiment when read in conjunction with the appended drawing figures.

SPECIFIC DESCRIPTION OF THE PREFERRED EMBODIMENT

Figure 5:
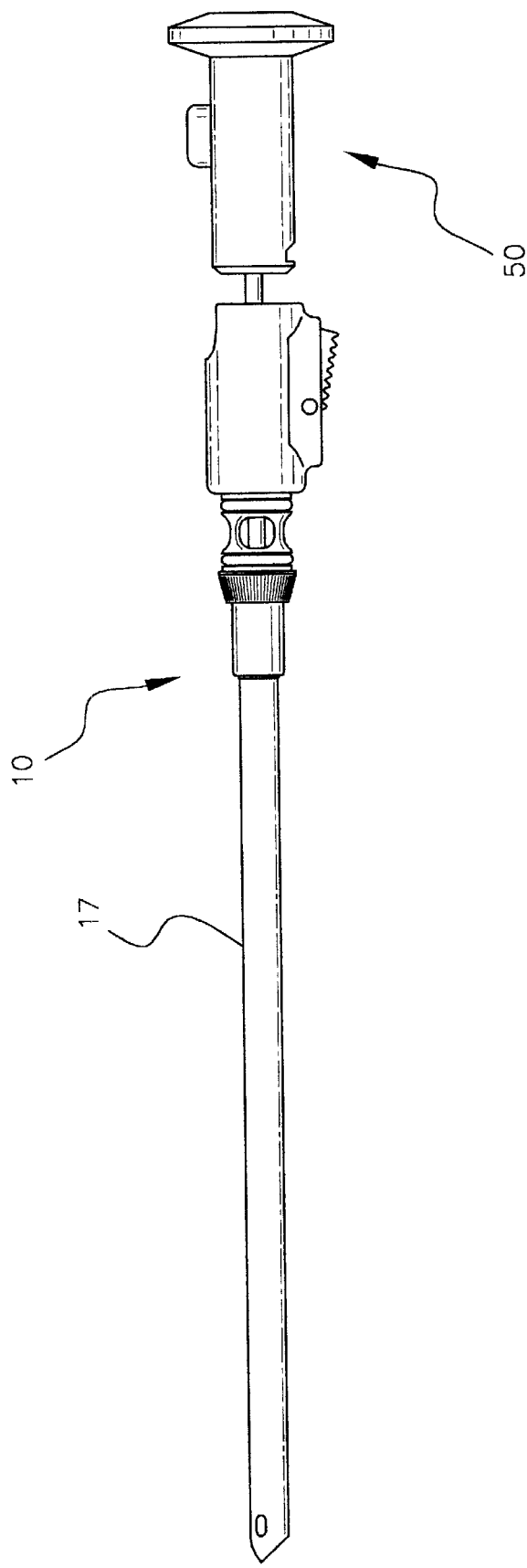
FIG. 5 shows a side view of the sheath with an endoscope partially installed therein.
Figure 6:
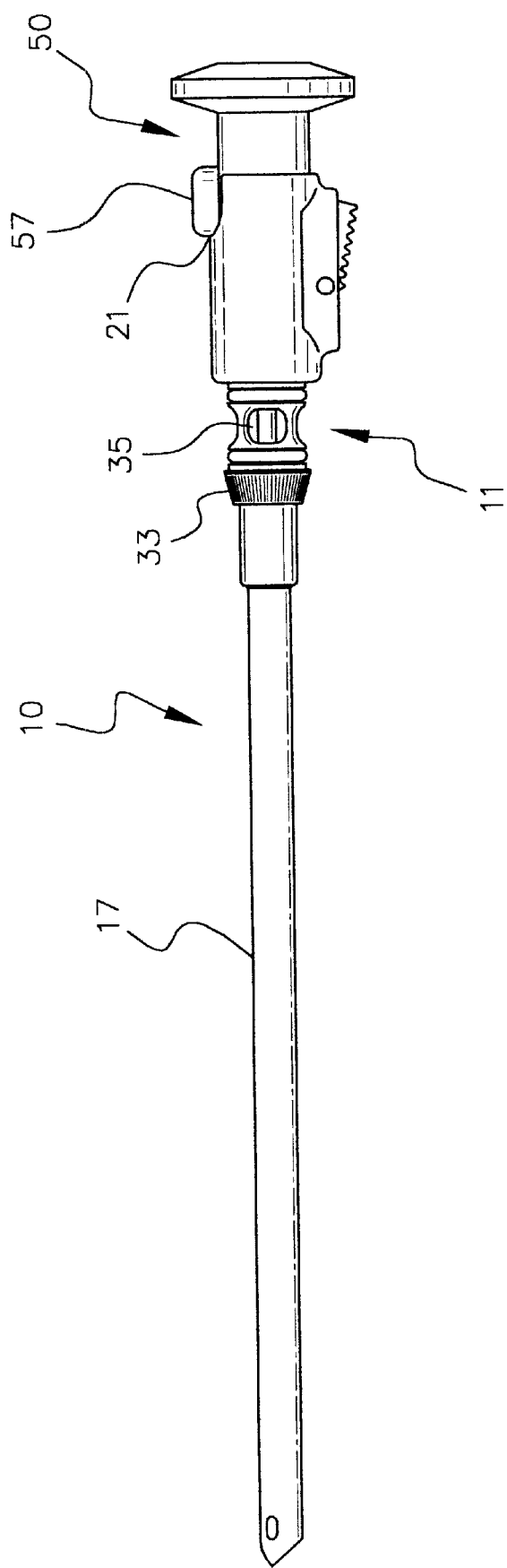
FIG. 6 shows a side view of a sheath with an endoscope completely installed therein.
Figure 7:
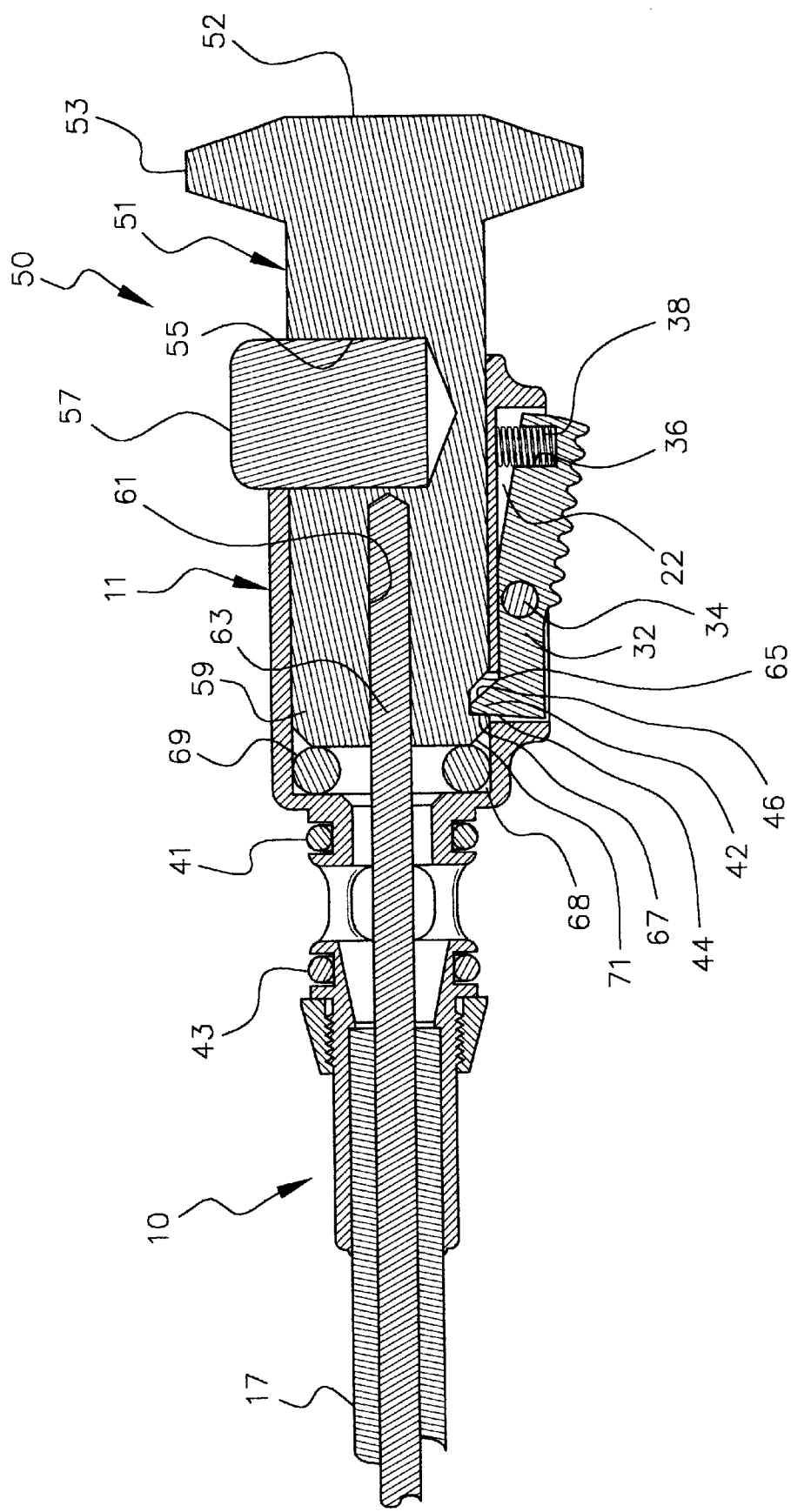
FIG. 7 shows a longitudinal cross-sectional view of the structure as shown in FIG. 6.

Reference is first made to FIGS. 1–4 which describe details of a sheath generally designated by the reference numeral 10 and seen to include a housing 11 having a proximal end 13 and a distal end 15 to which is affixed an elongated hollow tube 17 (see FIGS. 5–7).

With reference back to FIGS. 1–4, the housing 11 has an opening 19 at the proximal end 13 that includes a U-shaped notch 21 (FIG. 1) that includes proximal edges 23 and 25 that are substantially non-parallel, such that the notch diverges in the proximal direction. The distal end 15 of the housing 11 has a distal opening 27, smaller than the proximal opening 19 and allowing the endoscope (to be described in greater detail hereinafter) to pass therethrough. The distal end 15 includes a smooth cylindrical surface 29 terminating at its proximal end in a series of threads 31 designed to threadably receive a fitting 33 (FIGS. 5–7) to retain a valve assembly (not shown) over openings 35 as described below. Tube 17 is preferably welded to the housing 11 and is sized so as to define an elongated annular fluid channel (not shown) between its inner cylindrical surface and the exterior cylindrical surface of the endoscope.

Figure 1:
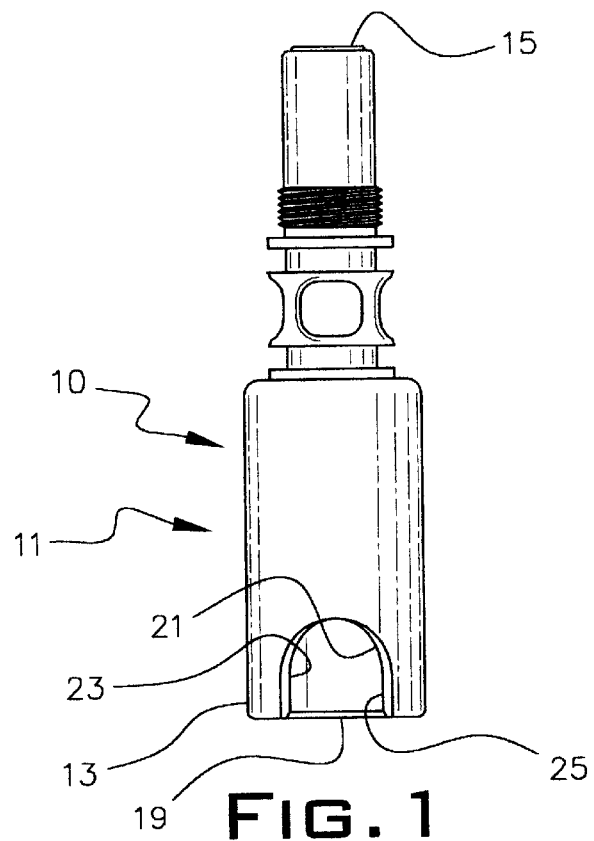
FIG. 1 shows a top view of a proximal end of a sheath designed to receive an endoscope.
Figure 2:
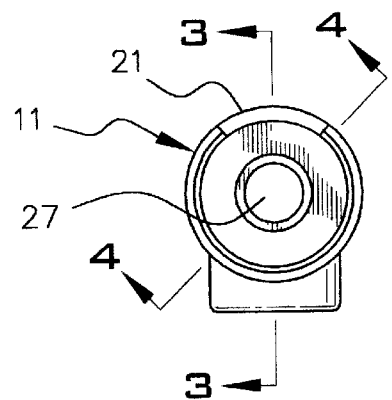
FIG. 2 shows an end view of the sheath of FIG. 1.
Figure 3:
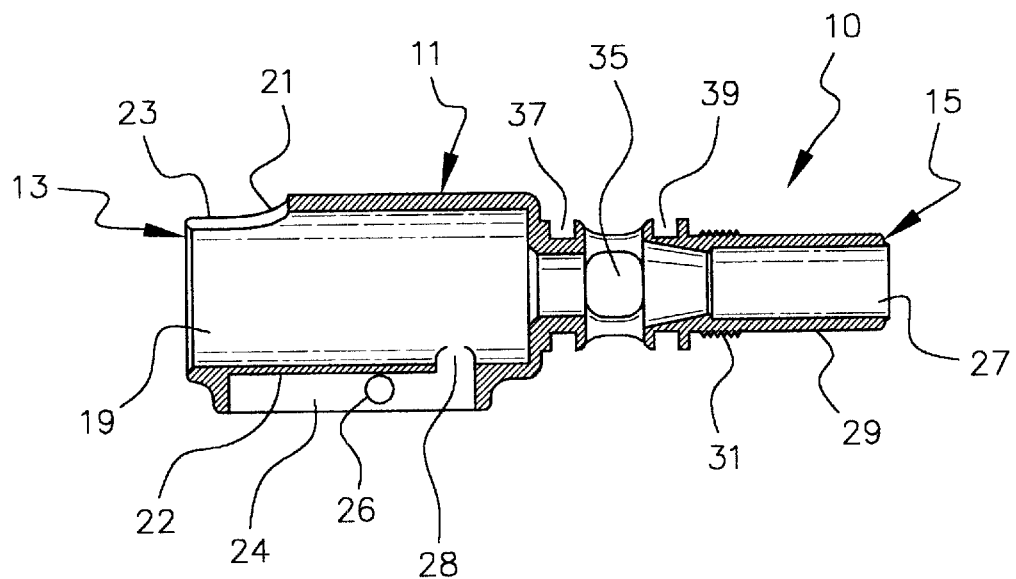
FIG. 3 shows a cross-sectional view along the line 3—3 of FIG. 2.
Figure 4:
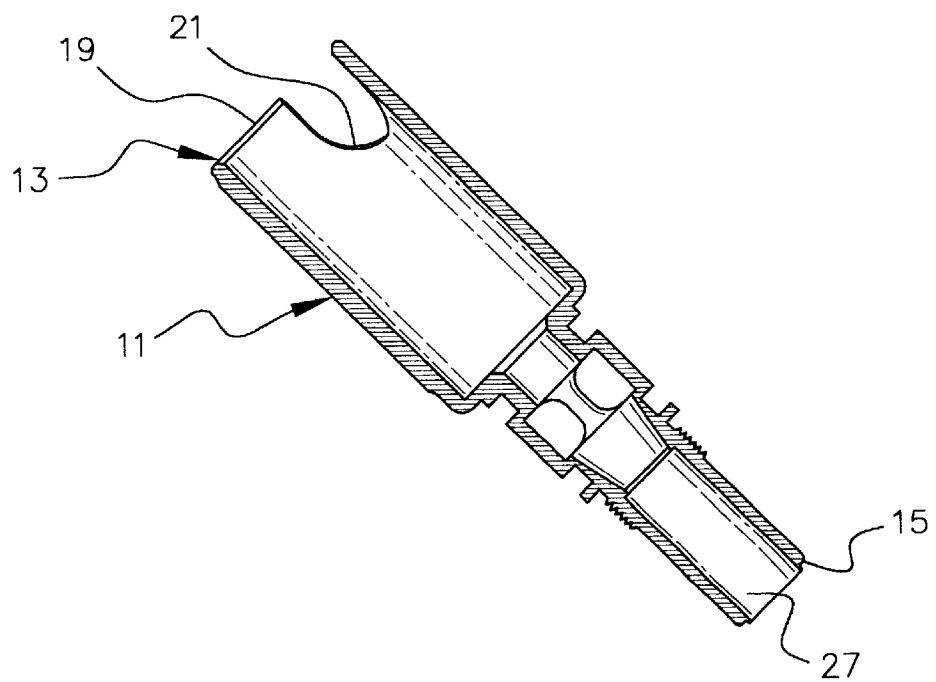
FIG. 4 shows a cross-sectional view along the line 4—4 of FIG. 2.

With particular reference to FIG. 3, intermediate the ends 13, 15 of the housing 11, openings 35 are provided and a proximal recess 37 is provided along with a distal recess 39. These recesses 37 and 39 are sized and configured to receive O-rings such as those designated by the respective reference numerals 41 and 43 in FIG. 7. These O-rings 41 and 43 seal the proximal and distal ends of a chamber formed by a valve assembly (not shown) that is slid over the openings 35 and includes structure overlying the O-rings 41 and 43 as is well known to those skilled in the art.

Reference is now made to FIGS. 5–7, wherein a description of the details of the endoscope most pertinent to the present invention will be made. Because only the exterior shape of an endoscope needs to be shown to explain the operation of the invention, FIG. 7 depicts sheath 10 in engagement with a schematically represented endoscope 50. Because the external components of an endoscope are equivalent to those of an obturator, with which sheath 10 also may be used, element 50 will be considered to represent an obturator as well as an endoscope and the various components of FIG. 7 will be described below in terms of an obturator. Such components will be identified also with their equivalent endoscope components where applicable. Thus, as noted above, obturator 50 schematically represents an endoscope as well. Obturator 50 (meaning also endoscope 50) has a proximal body housing 51 (meaning also endoscope housing 51) which includes an enlarged proximal end 52 (meaning also eyepiece 52) having a widened periphery 53 (meaning also eyecup 53). Body 51 further includes a bore 55 extending partially therethrough perpendicular to the longitudinal extend of body 51 and receiving a member simulating a light post 57 therein. Body 51 includes a distal end 59 having a recess 61 therein sized to receive the obturator shaft (meaning also endoscope body 63 which includes optics operatively connected by means not shown to eyepiece 52). In view of the above, any reference herein to endoscope or similar terminology will be deemed to interchangeably refer also to an obturator.

With reference back to FIG. 3, the sheath housing 11 has a recess 22 therein with a side wall 24 having an opening 26 therethrough. The housing has an opening 28 for a purpose to be described in greater detail hereinafter.

With reference back to FIG. 7, it is seen that the recess 22 of the sheath housing 11 receives a latch 32 having a pivot comprising a shaft 34 received within the opening 26. The latch has a proximal end with a counterbore recess 36 receiving a coil spring 38 that tends to bias the latch 32 in the clockwise direction of rotation in the view of FIG. 7. The distal end of the latch 32 has a finger 42 that is sized to be received within a notch 65 formed in the endoscope housing 51. The finger 42 of the latch 32 includes a flat distal surface 44 that engages a corresponding flat wall 67 of the notch. The interaction of the flat surface 44 and the flat wall 67 prevents the endoscope 50 from being moved out of the installed position shown in FIG. 7 unless the user rotates the latch 32 in the counterclockwise direction in the view of FIG. 7 against the biasing force of the spring 38 to remove the finger 42 from the notch 65. With the latch 32 in that position, the user may disconnect the endoscope 50 from the sheath 10. The present invention keeps the latch mechanism within the sheath housing 11 rather than in the endoscope housing 51, thereby minimizing the user's cost since a user would normally possess a small number of sheaths that could be used in conjunction with a larger number of endoscopes.

As also seen in FIG. 7, a resilient O-ring 69 is received within a recess 68 formed within the sheath housing 11. When the endoscope housing 51 is inserted into the sheath housing 11, the distal end 59 of the endoscope housing 51 engages the O-ring 69 to provide both a sealing and spring effect. This interaction provides substantial contact between the endoscope housing 51 and the sheath housing 11 to absorb leverage forces during use to minimize damage to the fragile optical elements contained within the endoscope body 63.

As best seen with reference to FIGS. 5 and 6, particularly FIG. 6, when the endoscope 50 is installed in the sheath 10, the light post 57 is fully received within the U-shaped notch 21 of the sheath housing 11, thereby effectively and reproducibly aligning the endoscope 50 within the sheath 10, both rotatably and longitudinally.

With further reference to FIG. 7, the distal end 59 of the endoscope housing 51 includes an angled shoulder 71. As the endoscope 50 is being inserted into the sheath 10, when the ramp surface 46 of the finger 42 engages the surface 71 of the endoscope housing 51, the interaction between these surfaces causes the latch 32 to pivot in the counterclockwise direction in the view of FIG. 7, thereby causing the finger 42 to ride up the surface 71 and into the notch 65, whereupon the endoscope 50 and sheath 10 are securely locked together.

Based upon the above description, as should be self-evident, when it is desired to install the endoscope 50 within the sheath 10, the distal end of the endoscope body 63 is inserted through the proximal opening 19 of the sheath housing 11 and is inserted through the distal opening 27 and motion is continued until the light post 57 of the endoscope housing 51 is received within the notch 21 formed on the proximal end of the sheath housing 11. As distal movement of the endoscope housing 51 continues, the distal end 59 of the endoscope housing engages O-ring 69 to provide a sealing spring effect and the surface 71 of the endoscope housing 51 engages the surface 46 of the finger 42 of the latch 32, thereby rotating the latch 32 in the counterclockwise direction in the view of FIG. 7 until the finger 42 enters the notch 65 of the endoscope housing 51 under the force exerted thereon by the spring 38. When it is desired to remove the endoscope 50 from the sheath 10, the portion of the latch 32 adjacent the spring 38 is depressed, thereby rotating the latch 32 in the counterclockwise direction in the view of FIG. 7, thereby releasing the finger 42 from the notch 65 of the endoscope housing 51. In that position of the latch 32, the endoscope housing 51 is pushed by the spring force of the O-ring 69 in the right-hand direction in the view of FIG. 7 and further motion in the same direction removes the endoscope 50 from the sheath 10.

As such, an invention has been disclosed in terms of a preferred embodiment thereof which fulfills each and every one of the objects of the invention as set forth hereinabove and provides a new and useful scope-sheath interface of great novelty and utility.

Of course, various changes, modifications and alterations in the teachings of the present invention may be contemplated by those skilled in the art without departing from the intended spirit and scope thereof.

As such, it is intended that the present invention only be limited by the terms of the appended claims.

What is claimed is:

1. In an endoscope and sheath assembly, said sheath having a sheath housing with a proximal end and a distal end, said proximal end having a proximal opening and said distal end having a distal opening, said endoscope having an endoscope housing with an endoscope body attached to a distal end of said endoscope housing, the improvement comprising:
   a) said proximal opening of said sheath housing having a notch extending distally therefrom in a peripheral wall of said sheath housing;
   b) said endoscope housing having a light post extending outwardly therefrom;
   c) said light post being receivable within said notch to align said endoscope within said sheath in a desired rotative and axial orientation.

2. The assembly of claim 1, wherein said endoscope housing has a longitudinal axis of elongation, said light post extending perpendicularly to said axis.

3. The assembly of claim 1, wherein said notch is U-shaped.

4. The assembly of claim 3, wherein said U-shaped notch includes proximal terminations that diverge from one another.

5. The assembly of claim 1, further including an O-ring received within said sheath housing, a distal end of said endoscope housing engaging said O-ring.

6. The assembly of claim 1, wherein said proximal opening has a larger diameter than a diameter of said distal opening.

7. The assembly of claim 1, further including latch means for releasably locking said endoscope housing within said sheath housing.

8. The assembly of claim 7, wherein said latch means comprises a notch formed in said endoscope and a latch mounted on said sheath housing.

9. The assembly of claim 8, wherein said latch is pivotable.

10. The assembly of claim 9, wherein said latch is resiliently biased in a latching direction.

11. The assembly of claim 9, wherein said latch includes a finger receivable within said endoscope notch.

12. The assembly of claim 11, wherein said latch is resiliently biased in a latching direction.

13. The assembly of claim 12, wherein said latch is resiliently biased with a compression spring.

14. An endoscope and sheath assembly, comprising:
   a) a sheath having a sheath housing with a proximal end and a distal end, said proximal end having a relatively large proximal opening and said distal end having a relatively small distal opening;
   b) said endoscope having an endoscope housing with an endoscope body attached to a distal end of said endoscope housing;
   c) said proximal opening of said sheath housing having a U-shaped notch extending distally therefrom in a peripheral wall of said sheath housing;
   d) said endoscope housing having a light post extending outwardly therefrom perpendicular to a longitudinal axis of said endoscope housing;
   e) said light post being receivable within said notch to align said endoscope within said sheath in a desired rotative and axial orientation.

15. The assembly of claim 14, wherein said U-shaped notch includes proximal terminations that diverge from one another.

16. The assembly of claim 14, further including an O-ring received within said sheath housing, a distal end of said endoscope housing engaging said O-ring.

17. The assembly of claim 14, further including latch means for releasably locking said endoscope housing within said sheath housing, said latch means comprising a notch formed in said endoscope and a pivotable latch mounted on said sheath housing.

18. The assembly of claim 17, wherein said latch is resiliently biased in a latching direction by a spring.

19. The assembly of claim 18, wherein said latch includes a finger receivable within said endoscope notch.

* * * * *